US010330580B2

(12) United States Patent
Min et al.

(10) Patent No.: US 10,330,580 B2
(45) Date of Patent: Jun. 25, 2019

(54) DYNAMIC MAGNETIC CELL SORTING

(71) Applicant: IMEC VZW, Leuven (BE)

(72) Inventors: Richard Min, San Jose, CA (US);
Liesbet Lagae, Leuven (BE);
Chengxun Liu, Leuven (BE);
Chengjun Huang, Leuven (BE)

(73) Assignee: IMEC VZW, Leuven (BE)

( * ) Notice: Subject to any disclaimer, the term of this patent is extended or adjusted under 35 U.S.C. 154(b) by 64 days.

(21) Appl. No.: 15/179,484

(22) Filed: Jun. 10, 2016

(65) Prior Publication Data

US 2016/0370279 A1    Dec. 22, 2016

(30) Foreign Application Priority Data

Jun. 17, 2015   (EP) .................................... 15172487

(51) Int. Cl.
*G01N 15/10*    (2006.01)
*B01L 3/00*    (2006.01)
(Continued)

(52) U.S. Cl.
CPC .... *G01N 15/1031* (2013.01); *B01L 3/502715* (2013.01); *B01L 3/502761* (2013.01); *B03C 1/01* (2013.01); *B03C 1/0332* (2013.01); *B03C 1/0335* (2013.01); *B03C 1/288* (2013.01); *G01N 15/1056* (2013.01); *B01L 2200/0652* (2013.01); *B01L 2300/06* (2013.01); *B01L 2300/0864* (2013.01); *B01L 2300/12* (2013.01); *B01L 2400/043* (2013.01); *B03C 2201/18* (2013.01); *B03C 2201/26* (2013.01);
*G01N 35/0098* (2013.01); *G01N 2015/1081* (2013.01); *G01N 2015/149* (2013.01)

(58) Field of Classification Search
USPC .............................. 422/73, 502–504; 436/10
See application file for complete search history.

(56) References Cited

U.S. PATENT DOCUMENTS 6,858,184 B2 *   2/2005   Pelrine ................. B01J 19/0046
                                                            204/193
9,220,831 B2 * 12/2015   Ingber ..................... A61M 1/36
(Continued)

FOREIGN PATENT DOCUMENTS

WO    WO-0040947 A1 *    7/2000    ............... B03C 1/01
WO    WO-2007044642 A2 *  4/2007    ............... A61M 1/36
WO    WO-2012004363 A2 *  1/2012    ........ G01N 27/44756

OTHER PUBLICATIONS

Liu, Chengxun et al., "Cell Manipulation With Magnetic Particles Toward Microfluidic Cytometry", Journal of Applied Physics, vol. 105, 2009, pp. 102014-1-102014-11.

*Primary Examiner* — Dean Kwak
(74) *Attorney, Agent, or Firm* — McDonnell Boehnen Hulbert & Berghoff LLP (57) ABSTRACT

A microfluidic magnetic selector comprises a microfluidic channel comprising at least one bifurcation, forming a selection portion of the selector and splitting the microfluidic channel into a main channel and at least one selection channel; at least one magnetic flux concentrator for concentrating a magnetic flux at the level of the bifurcation, and means for generating a magnetic field within the magnetic flux concentrator, and a controller for controlling magnetic pulses through the magnetic flux concentrator.

12 Claims, 2 Drawing Sheets

(51) Int. Cl.
  *B03C 1/01*   (2006.01)
  *B03C 1/033*  (2006.01)
  *B03C 1/28*   (2006.01)
  *C40B 60/14*  (2006.01)
  *G01N 35/00*  (2006.01)
  *G01N 15/14*  (2006.01)

(56) References Cited

U.S. PATENT DOCUMENTS

| | | | | |
|---|---|---|---|---|
| 2001/0052769 | A1* | 12/2001 | Simmonds | B82Y 15/00 |
| | | | | 324/204 |
| 2008/0302732 | A1* | 12/2008 | Soh | B01L 3/502761 |
| | | | | 210/695 |
| 2009/0047297 | A1* | 2/2009 | Kim | B03C 1/288 |
| | | | | 424/184.1 |
| 2009/0212768 | A1* | 8/2009 | Llandro | B01L 3/502761 |
| | | | | 324/228 |
| 2010/0188076 | A1* | 7/2010 | Kahlnnan | G01N 27/745 |
| | | | | 324/232 |
| 2012/0077184 | A1* | 3/2012 | Hu | B01L 3/50273 |
| | | | | 435/5 |
| 2012/0295366 | A1* | 11/2012 | Zilch | B01L 3/502761 |
| | | | | 436/501 |
| 2013/0004982 | A1* | 1/2013 | Bar | G01N 15/1031 |
| | | | | 435/29 |
| 2014/0174994 | A1* | 6/2014 | Bemate | B01L 3/502753 |
| | | | | 209/155 |

* cited by examiner

DYNAMIC MAGNETIC CELL SORTING

CROSS-REFERENCE TO RELATED APPLICATIONS

The present application is a non-provisional patent application claiming priority to European Patent Application No. EP 15172487.9, filed Jun. 17, 2015, the contents of which are hereby incorporated by reference.

FIELD OF THE DISCLOSURE

The present disclosure relates to the field of cytometry and particle sorting. More specifically it relates to a magnetophoretic flow sorting method and device.

BACKGROUND

Cytometry and cell separation are very important in several fields like biochemistry, bioengineering and medicine. For example, in oncology, detection and analysis of even a single tumor cell is a fundamental step in diagnosis and treatment of different types of cancer. Several methods have been provided, for example optical analysis of a stained sample under a microscope (optical cytometry), attachment of cells to rare earth elements, ionization and cell separation (mass cytometry), etc.

These techniques require usually bulky and expensive equipment, and sometimes the sample preparation and analysis is lengthy and, in case of optical cytometry, not always reliable due to the limited amount of sample available to analyze.

Modern techniques include flow cytometers, which are able to analyze large amounts of particles in a relatively short time. Typically, the particles are labelled (for example, by staining) and included in a solution which is introduced in microfluidic channels, and lasers and/or fluorescence are used for studying the type and/or number of particles flowing in the solution. The main disadvantage of flow cytometry is potential overlapping of labels, making the analysis of the results less reliable and effective than, for example, mass cytometers.

Other types of cytometry use magnetic fields, for example magnetic twisting cytometry. In this technique, magnetic particles are attached to for example blood cells and viscoelastic effects are studied, for instance via optical means.

Magnetic force can also be used for cell separation. In "Cell manipulation with magnetic particles toward microfluidic cytometry" (Liu et al., J. Appl. Phys. 105, 102014 (2009)), magnetophoresis is proposed for cell separation in a microfluidic channel. The reference takes into account mixtures of target particles to be selected and non-target particles, both of which may present magnetic properties (for example, a solution of particles labelled with magnetic particles mixed with loose magnetic particles). The magnetic separation is performed with a gradient of a magnetic field, but this method either presents a low efficiency and reliability or results in problems like blocking of trap sites, aggregation and channel clogging, as well as heating problems.

SUMMARY

It is an object of embodiments of the present disclosure to provide a fast, efficient and reliable method, and a corresponding device, for continuous separation of particles from a solution.

The above objective is accomplished by a method and device according to the present disclosure.

In a first aspect, embodiments of the present disclosure relate to a microfluidic magnetic selector comprising a microfluidic channel. The channel comprises at least one bifurcation, forming a selection portion of the selector and splitting the microfluidic channel into a main channel and at least one selection channel. Embodiments of the present disclosure are not limited to a single selection channel, and the microfluidic channel may be split into a main channel and two or more selection channels. The microfluidic magnetic selector further comprises at least one magnetic flux concentrator for concentrating a magnetic flux at the level of the bifurcation. It also comprises means for generating a magnetic field within the magnetic flux concentrator, and a controller for controlling magnetic pulses through the magnetic flux concentrator.

Some embodiments of the present disclosure provide that control of a microfluidic magnetic selector can be done with a strong magnetic field avoiding vessel clogging and heating by allowing high-frequency pulsing. Such pulsing may provide selection between different particles in the microfluidic channel and may guide particular types of particles in a particular direction, for example separating magnetically tagged particles from a fluid containing a mixture of target and non-target particles, and improving separation of target tagged particles from mistagged particles and other magnetically active particles (e.g. unattached microbeads).

In particular embodiments of the present disclosure, the magnetic flux concentrator may comprise a ferromagnetic material with a saturation magnetization of at least 0.5 Tesla. In some embodiments of the present disclosure, the speed of transition between saturated field and null field may be increased by using for example hard magnetic materials. The present disclosure may not be limited thereto, and soft magnetic materials may also be used, which may provide increased control over the magnetic field amplitude.

In particular embodiments of the present disclosure, the at least one magnetic flux concentrator may comprise a tip which may be small with respect to the rest of the flux concentrator body; for example the tip may have a dimension between 10 nm and 0.1 mm. Some embodiments of the present disclosure provide that Anisotropic Magneto-Resistive or Giant Magneto-Resistive heads can be used, reaching very high magnetic flux and field density at the tip of the head, allowing an accurate or even individual selection of target particles.

The microfluidic magnetic selector according to particular embodiments of the present disclosure may be an integrated circuit or may be part of one; the present disclosure, however, not being limited thereto. Such an integrated circuit may be manufactured using standard semiconductor manufacturing technology, improving its integration with other devices and compactness.

Further, the magnetic flux concentrator may be located in the connection between the microfluidic channel and at least one selection channel in embodiments of the present disclosure. Some embodiments of the present disclosure provide that the amount of target molecules returning to the microfluidic channel from the bifurcation can be reduced. Embodiments of the present disclosure comprise the tip of the magnetic flux concentrator being closest to the connection between the microfluidic channel and at least one selection channel, for example at the corner between the main channel and the selection channel.

Even further, the magnetic flux concentrator may comprise conducting coils, for example surrounding the magnetic flux concentrator, as a means for generating a magnetic field in particular embodiments of the present disclosure. Some embodiments of the present disclosure provide that the magnetic field may be easily controlled by means of a compact magnetic source.

In a second aspect, embodiments of the present disclosure relate to a method for magnetic selection of target particles, the method being suitable for being applied to a microfluidic magnetic selector according to embodiments of the first aspect of the present disclosure. The method comprises providing a fluid comprising at least one target particle exhibiting magnetic behavior, for example ferromagnetic, or paramagnetic, or superparamagnetic behavior, the present disclosure not being limited thereto. In certain embodiments of the present disclosure, the target particles may be inherently magnetic. In some embodiments, the magnetic properties of the target particles may be conferred and/or tuned by the addition (e.g. attachment) of at least one ferromagnetic, superparamagnetic or paramagnetic bead. The method further comprises flowing of the fluid through a microfluidic magnetic selector, e.g. a selection portion comprising a microfluidic channel and at least one bifurcation, and splitting the microfluidic channel into a main channel and at least one selection channel, and at least one magnetic flux concentrator pulsing magnetic flux through the at least one magnetic flux concentrator and into the flowing fluid. The method further comprises, by means of the magnetic flux, deflecting the at least one target particle through the at least one bifurcation into the at least one selection channel. Some embodiments of the present disclosure provide that separation of target particles from other particles can be dynamical. Some embodiments of the present disclosure provide that heating or vessel clogging can be reduced or avoided, which may be useful in miniaturized devices such as microfluidic devices. Some embodiments of the present disclosure provide that any type of target particle and cell can be a tagged particle showing analogous behavior as ferromagnetic, paramagnetic or superparamagnetic particles. While ferromagnetism and ferrimagnetism are commonly known in macroscopic effects of particles (e.g. beads) composed of multi-domains, in embodiments in which the particle or bead size is smaller than a single magnetic domain size, the particle or bead may be paramagnetic or superparamagnetic, and thus may be configured to have a high relaxation speed. Hence, due to their fast reaction to an external magnetic field, paramagnetic or superparamagnetic particles (e.g. beads, like microbeads or nanobeads) may be used in various embodiments, the present disclosure not limited thereto.

Embodiments of the present disclosure may further comprise estimating the average momentum of the at least one target particle (e.g. by calculations of fluid dynamics using the mass and volume of the particle, or by sensors), and then pulsing magnetic flux through the magnetic flux concentrator at a frequency such that the at least one target particle can be deflected through the at least one bifurcation into the selection channel, while any other particle in the fluid may not be deflected through the at least one bifurcation. Some embodiments of the present disclosure provide that the frequency of the magnetic flux can be tuned for selection of target particles (e.g. circulating tumor cells, CTCs) from other tagged but non-target cells, according to weight and/or number of linked magnetic beads, providing the method with dynamic magnetic selection. Additionally or alternatively, the amplitude of the magnetic field can also be controlled, hence pulsing magnetic flux with a magnetization field strength, also participating in deflection of at least one target particle through the at least one bifurcation into the selection channel, while other particles in the fluid may not be deflected through the at least one bifurcation. Some embodiments of the present disclosure provide that the strength of the field can be adjusted to the fluid speed.

In particular embodiments of the present disclosure, pulsing magnetic flux comprises alternating the magnetic flux concentrator with a magnetic field amplitude stronger than the coercivity field. Hence, the magnetic flux may be pulsed with a magnetic field amplitude stronger than the coercivity field of the magnetic flux concentrator. Some embodiments of the present disclosure provide that the device can be operated between maximum field and zero field with little or no calibration.

Some embodiments of the second aspect of the present disclosure may comprise pulsing magnetic flux at frequencies between 0.1 MHz and 1 GHz. Some embodiments of the present disclosure provide a high frequency and gradient, which may improve selection of target cells.

Particular aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the embodiments described herein.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of embodiments of the present disclosure, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed subject matter requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the present disclosure, and form different embodiments, as would be understood by those in the art. For example, in the following claims, any of the claimed embodiments can be used in any combination.

In the description provided herein, numerous specific details are set forth. However, it is understood that embodiments of the present disclosure may be practiced without these specific details. In other instances, well-known methods, structures and techniques have not been shown in detail in order not to obscure an understanding of this description.

A "microfluidic channel" is, within the meaning of the present disclosure, a capillary or a conduit in a device, having a cross-section wide enough so as to allow circulation of particles in a fluid suspension. In some embodiments of the present disclosure, a microfluidic channel may comprise meanders, bifurcations, charge and discharge zones, etc. In some embodiments of the present disclosure, a microfluidic channel may be etched in a substrate made from any suitable material like glass, a polymer or a semiconductor material, although the present disclosure is not limited thereto.

A "bifurcation" in the context of the present disclosure may include a location where a microfluidic channel splits into at least two microfluidic channel branches: a main channel and at least one selection channel.

Where in embodiments of the present disclosure reference is made to a "magnetic flux concentrator", reference is made to a strong localized magnetic field source comprising a magnetic field source (e.g. a coil and a core, a moving permanent magnet, etc.) and a means for concentrating the magnetic flux, so as to obtain a high magnetic flux on a limited volume of a microfluidic channel. The means for concentrating the flux may for example be one or more protrusions or attached additions to a magnetic field source, referred to as a "pole" or "poles", and having a reduced sectional area. In particular embodiments, the means for concentrating the flux may e.g. be a magnetic head. The reduced cross-sectional area allows an increase of the flux. In some embodiments of the present disclosure, the area of a pole cross-section may be smaller than the width of the microfluidic channel, for example it may be of the same order of magnitude as the average diameter of the particles to be separated, but it may also be smaller. For example the cross-section may be bigger than 10 nm but smaller than 0.1 mm. The magnetic flux concentrator can be connectable to other devices, such as a current pulse generator, a controller, etc., and it can be a single piece or it can comprise multiple parts.

Where in embodiments of the present disclosure reference is made to a "magnetic bead" or MB, reference is made to a bead, for example a coated micro- or nanoparticle used to tag or label globules, cells or in general particles. It is said that a particle or cell is tagged if one or more magnetic beads are attached to said particle or cell. The magnetic properties of the MBs (for example superparamagnetism and magnetic susceptibility, among others) determine the behavior of the target particles, as the main function of the MBs is to confer determined magnetic properties to the particle they are attached to (which receive the name of the "tagged particle" or "tagged cell"). For example, MBs may comprise ferri- or ferromagnetic materials if the size is big enough for magnetic domains to form, or for example MBs may comprise nanocrystalline materials. In some embodiments of the present disclosure, the MBs may show paramagnetic or superparamagnetic properties, so the magnetic dipoles are induced only with externally applied magnetic field, and are null if no field is applied. Due to their fast reaction to an external magnetic field, paramagnetic or superparamagnetic particles (e.g. beads, like microbeads or nanobeads) may be used in some embodiments; the present disclosure, however, not being limited thereto.

The magnetic beads may comprise a coating for conferring a determined affinity (for example chemical affinity) for a determined type of particles, namely "target particles" or "target cells", and show less or no affinity for the remainder of particles, the "non-target particles". In some cases, target particles present suitable inherent magnetic properties (e.g. red blood cells show paramagnetism), in which case the use of MBs may be reduced or avoided.

A "mistagged particle" is a non-target particle that has at least one MB attached.

In a first aspect, the present disclosure relates to a microfluidic device for separation of particles with pre-determined magnetic properties. The microfluidic device comprises a microfluidic channel and at least one bifurcation, forming a selection portion of the device and splitting the microfluidic channel into a main channel and at least one selection channel or duct.

The microfluidic device according to embodiments of the present disclosure comprises a magnetic flux concentrator, which may be connectable to a controller, for producing strong localized magnetic pulses in a limited region of the microfluidic channel.

In embodiments of the present disclosure, a microfluidic channel may have a width between 10 μm and 2 mm and a height between 5 μm and 2 mm. Its length may be several times its width, for example at least twofold, but often much longer. The microfluidic channel may extend to other parts of the device. The at least one selection duct may have the same dimension as the main channel, but it can also be smaller, for example it can be narrower than the main channel.

The selection portion can be located at the bifurcation under a right angle with respect to the main channel, or it may form an acute or obtuse angle with respect to the main channel in the direction of flow. Some embodiments may comprise for example two bifurcations, hence comprising two ducts connected to the main channel. For example, one of the ducts may form an acute angle with respect to the main channel and the other duct may form an obtuse angle. Any other suitable combination of angles is possible. A change of direction of the main channel in the selection portion is also possible.

A magnetic flux concentrator may be present adjacent the at least one bifurcation. In some embodiments, the bifurcation can also comprise a magnetic flux concentrator as defining the walls of at least part of the selection and main channels.

The flux concentrator may be part of an integrated microfluidic device. It comprises at least one tip or pole which concentrates magnetic field flux. The cross-sectional shape of the tip may be circular, oval, rectangular, polygonal, or may be of any other suitable shape, and its area may be much smaller than the cross-sectional area of the microfluidic channel. For example, a cross-sectional dimension, e.g. diameter, of the tip may be bigger than 10 nm and smaller than 0.1 mm, for example it may be between 20 nm and 20 μm (micrometers). The magnetic field may be created for example in a core bulk comprising the pole. The core and the pole may form a single piece, or may consist of different parts. The flux concentrator may comprise materials with a high saturation, for example a saturation magnetization of at least 0.5 Tesla. It may comprise hard or soft ferromagnetic materials. The choice of material is of importance, as it has an influence on the induced magnetic field and on the range of values of the magnetic field available in normal operation of the device. Suitable hard magnetic materials are for example CoFe, CoFeB. In these cases, the flux concentrator usually operates between two different values of the magnetic field. Nonetheless the present disclosure is not limited thereto and other materials may be chosen. For example, if soft magnetic materials are used (SiFe, NiFe, etc), the magnetic remanence can be very small, so regulation of the current allows the generation of magnetic fields within a range of amplitudes. Either with hard or soft magnetic materials, in general, the aim of tuning the switching frequency is to control the response of the target molecules. A magnetic flux concentrator may comprise several poles, for example in several parallel microfluidic channels, providing substantially the same magnetic force in each of the channels.

In some embodiments of the present disclosure, the magnetic flux concentrator may comprise anisotropic magnetoresistive (AMR) or giant magnetoresistive (GMR) materials.

The magnetic field may be induced in the core bulk of the flux concentrator by means of conductive coils, for example copper, aluminum, gold, platinum or tungsten coils, at least partially wound around the core. A current pulse generator is connectable to the coils on the one hand, and to a controller for controlling the pulse generator on the other hand. The coils may also be partially wound around the selection duct, thus inducing magnetic force along a part of the selection duct and reducing the amount of tagged particles moving back to the main channel. Alternatively, the magnetic field may be provided by a movable (e.g. rotatable) permanent magnet, connectable to a controller for controlling the speed of rotation of the magnet. Any other system of obtaining a variable magnetic field of a suitable frequency can be used in embodiments of the present disclosure.

The magnetic field may be tuned by means of the controller, for example by controlling the strength and frequency of the current pulses through induction coils. The magnetic flux can be used for the magnetic separation of, for example, particles or cells whose magnetic properties are conferred by, for example, attachment to one or more ferromagnetic beads, for example MBs, micro-MBs or nano-MBs. The attachment may have for example a chemical nature (e.g. a chemical bond such as van der Waals interactions), for example attachment to a surface receptor of a target cell or to any chemical moiety of a target particle.

In certain embodiments of the present disclosure, the magnetic flux concentrator may output pulses with different frequencies and/or amplitudes. For example, it may produce pulses with two different frequencies, and for example two different amplitudes, which can be tuned by means of the controller. Such set-up may be useful for separating different types of target particles (e.g. of different size). In this case, two ducts can be connected to the main channel in the selection portion. The two ducts may have the same cross-sectional size, or different cross-sectional sizes determined by the sizes of the two sets of target particles.

In some embodiments of the present disclosure, more than one flux concentrator may be provided at the bifurcation, for example one flux concentrator next to each duct. For example, the flux concentrators may comprise the same materials and dimensions, or may be different, for example one of the concentrators may comprise hard magnetic materials while the other may comprise soft magnetic materials. The pulses may be different, for different types of target (tagged) particles. The concentrators may be located sufficiently apart from one another, to avoid interference. For example, they may be 5 times the width of the concentrator head apart from each other, although other distances are also possible.

Figure 1:
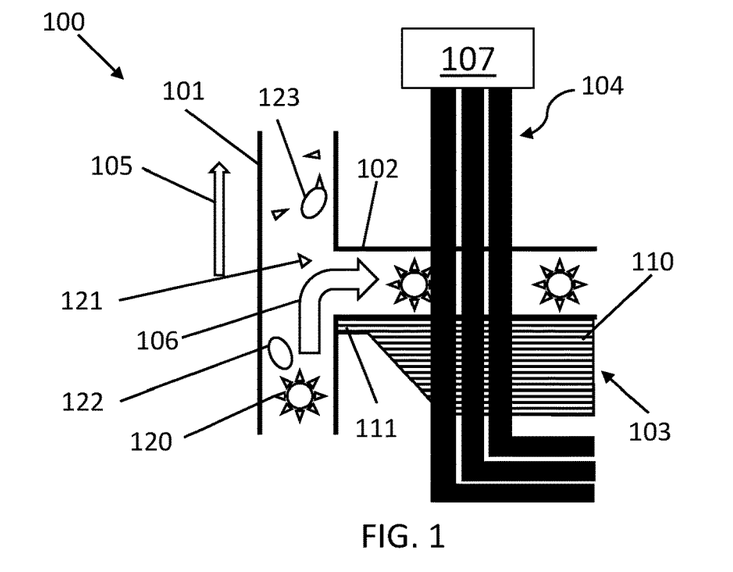
FIG. 1 schematically illustrates part of a microfluidic device for particle selection according to embodiments of the present disclosure, comprising a main channel, a selection channel and a magnetic flow concentrator.

FIG. 1 shows one embodiment of the present disclosure according to a first aspect of the present disclosure. A microfluidic selector 100 comprises a microfluidic channel 101 and a selection channel or duct 102 forming a bifurcation in a selection portion adjacent to a magnetic flux concentrator 103, which comprises a core 110 and a pole 111. For example, the core 110 may be surrounded by coils 104. The coils 104 may be connected to a control unit 107, which controls the electric current in the coils 104 for inducing a magnetic field within the core 110, which may then be concentrated in the pole 111, creating a strong magnetic field in a small region of the microfluidic channel 101 next to the selection channel or duct 102 which defines the selection portion. The microfluidic channel 101 may contain a solution, flowing according to the direction indicated by a straight arrow 105 in the microfluidic channel 101 or flowing in the direction indicated by a curved arrow 106 into the selection duct 102. The solution may comprise target tagged particles 120, loose (unattached) MBs 121, and non-target particles 122, some of which may be tagged 123.

Figure 2:
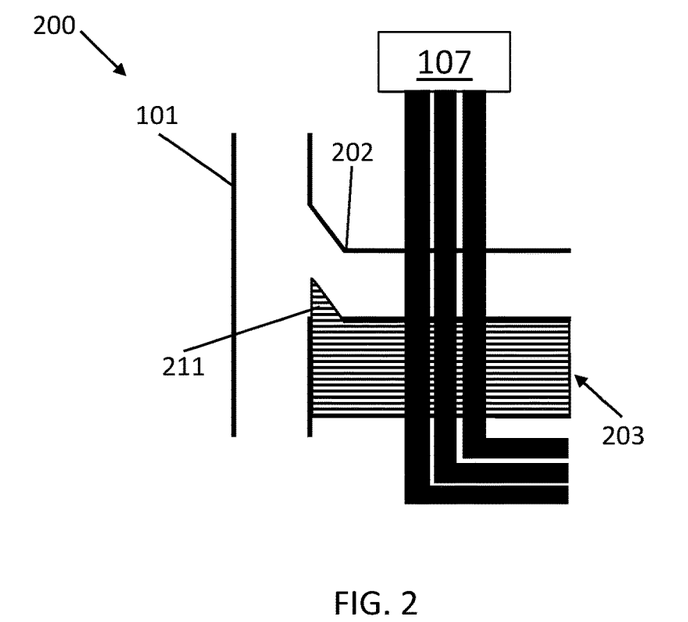
FIG. 2 schematically illustrates part of a microfluidic device according to embodiments of the present disclosure, comprising a selection channel forming an acute angle with the main channel.

Another possible channel configuration can be seen in FIG. 2. The microfluidic selector 200 comprises, as before, a bifurcation, but in this embodiment the selection duct 202 forms an acute angle with the microfluidic channel 101, and the pole 211 of the magnetic flux concentrator 203 presents a wedge shape.

Figure 3:
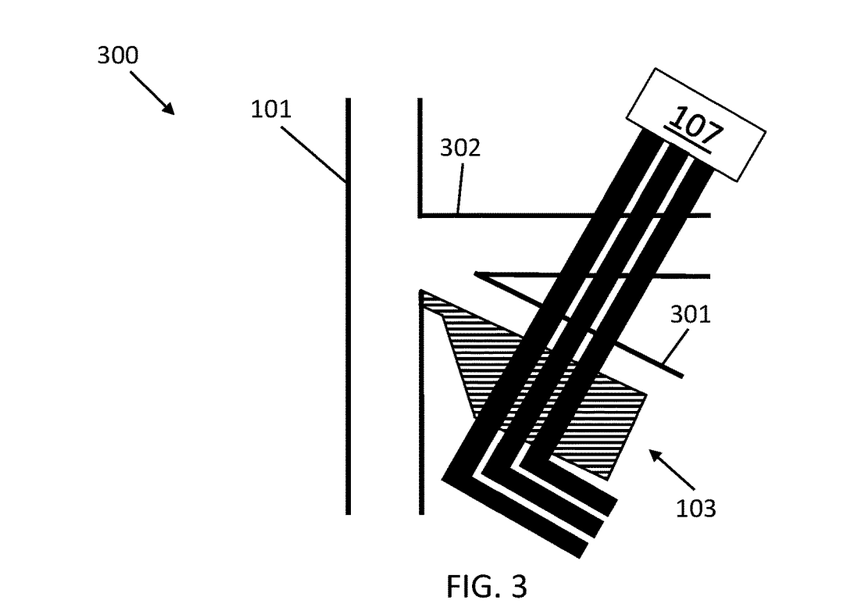
FIG. 3 schematically illustrates part of a microfluidic device for particle selection according to embodiments of the present disclosure, comprising a main channel and two selection channels.

In another possible configuration, FIG. 3, the microfluidic selector 300 comprises two selection ducts 301, 302 which are connected to the microfluidic channel 101. The ducts 301, 302 may have the same width, or their width may differ depending on the envisaged applications. For example, one of the ducts may allow the passage of small magnetic particles, such as unattached MBs, and the other may allow the passage of target particles. In FIG. 3, the selection duct 301 forms an acute angle with respect to the microfluidic channel 101 and the other duct 302 may form a right angle, but other configurations and angles are also possible.

In a second aspect, the present disclosure relates to a method of particle separation, via magnetophoresis, using microfluidic selectors according to embodiments of the first aspect of the present disclosure.

The method is suitable for separation of cells, virus, or particles in general which have pre-determined magnetic properties, in a solution flowing through a microchannel. The magnetic properties of the target molecules may be intrinsic (for example iron-bearing particles or cells, as for instance red blood cells), or may be externally conferred by attachment of one or more magnetic beads, e.g. micro- or nano-MBs.

The solution may in general comprise target particles with pre-determined magnetic properties, target particles without these magnetic properties, non-target particles and transport liquid, for instance comprising water, plasma, buffer solution, etc. Methods for obtaining these solutions are known in the art. Methods according to embodiments of the present disclosure are suitable for separation of intrinsically magnetic target particles from non-magnetic, non-target particles in a solution. Such methods are also suitable for separation of particles in which target particles are intrinsically non-magnetic. In such case, binding of target particles (or target cells) with magnetic beads (MBs) may be performed following known methods. Optimized mixing and binding methods may lead to a solution in which all or almost all target particles display pre-determined magnetic properties (via adhesion of a pre-determined number of MBs within a predetermined range, due to high affinity between target particles and MBs) and non-target particles not showing the same magnetic properties (as no MBs, or less MBs, may be attached to non-target particles due to lower affinity than with target particles). MBs can comprise superparamagnetic, ferromagnetic, ferrimagnetic or paramagnetic materials, which may be coated by a polymer and/or linked to specific antibodies. An example of solution treatment may comprise providing a pre-determined amount of magnetic beads with a suitable coating (e.g. micro- or nanocrystals of iron oxide, comprising appropriate receptors for the target particles) in the solution, hence obtaining a solution of mainly tagged target particles showing determined magnetic properties. In general, a MB is considered to be suitable if it shows great affinity with target particles and little or no affinity with non-target particles.

The present disclosure is not limited to one type of target and one type of MB. For example, it may be used to separate different types of target particles from a solution, for example by adding a type of MB suitable for both targets, or by adding different types of MBs each suitable for a different type of target particle, if the characteristics of the targets are such that it can be ensured that different particles present distinct mobilities during sorting.

In embodiments of the present disclosure, a magnetic field is pulsed between at least two values, at a pre-determined amplitude, frequency and pulse width, for separation of target particles from a medium. The target particles are characterized by a narrow specific profile of size, mass and interaction with the magnetic field.

Several interactions govern the movement of the particles in the solution. For example, the viscosity of the medium plays a role in the hydrodynamic drag force, defined by the viscosity of the medium $\eta$, the velocity $v$, and the hydrodynamic size $D$.

$$F_d = -3\pi \cdot D \cdot \eta \cdot v$$

Also other influences can be taken into account. The interaction of the small charges on the particles' surfaces can be described by the Derjaguin-Landau-Verwey-Overbeek (DLVO) force. Brownian motion from collisions between the particles and the molecules of the liquid medium is a contribution, producing large displacements on small particles (e.g., micrometric or submicrometric particles) but affecting also large particles. Buoyancy and gravity are also influential, playing a role in sedimentation. The movement of particles very close to a microfluidic wall may be taken into account by introducing a factor $f_D$ in $F_d$. The interaction of all these forces, together with the flow rate of the solution within the microfluidic channel, should be taken into account for the determination and optimization of the required or desired strength of the magnetic flux.

The magnetic force on a single (magnetic) particle can be calculated from the applied magnetic field B, from difference of volume magnetic susceptibility between the particle and the medium $\Delta\chi$, the volume of the particle $V_m$ and the permeability of vacuum $\mu_0$ $$F_{mag} = \frac{\Delta\chi V_m}{\mu_0}(B \cdot \nabla B)$$

All these forces scale as a function of the size of the magnetic particle.

The movement of the target particles under the magnetic force has a strong dependency on their magnetic character. In case of particles with MBs attached, the magnetic force applies to each of the MB attached to it, hence the movement of the particle depends of the amount of MBs attached. A particle with less MB attached, or loose MBs, will suffer different displacement.

Applying a constant magnetic field or a slowly alternating field usually results in clogging. The inventors have found that, in order to avoid this, a magnetic field may be applied in pulses with a pre-determined frequency and with a pre-determined pulse width, additionally reducing heating of the device.

Figure 4:
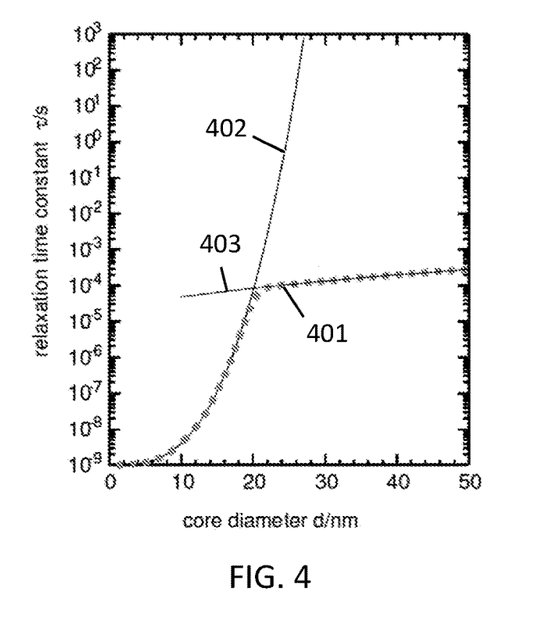
FIG. 4 shows a graph of the relaxation time constant as a function of the size of magnetic beads.

The width of the pulse (the minimum time period during which a pulse will be applied) can be tuned. FIG. 4 shows a graph with possible values for the relaxation time constant as a function of the diameter of the MBs. The relaxation time constant characterizes the time needed by a particle to reach the magnetic moment corresponding to the external magnetic field. Hence, the width of the magnetic pulse should be the same or higher than the relaxation time constant. If the time is too short, the particle will not have time to gain moment. As seen in the graph, the relaxation time depends of the size of the magnetic particle (e.g. the size of the MB), and the effective relaxation 401 changes drastically around 20 nm due to the combination of the Néel relaxation 402 and the Brownian relaxation 403 for the hydrodynamic diameter D.

The frequency of the magnetic field to be applied may be determined by the relaxation time and by the target particle. For example, it may be determined by the relaxation time of the MBs, by the size of the target particle and the number of MBs attached to it. Too low frequencies cause clogging, but too high frequencies may not let the target particles gain enough momentum. In typical applications of cell sorting, the frequency may take a value between 0.1 MHz and 1 GHz.

The pulses may make the magnetic field vary within a range of values, and in some cases these values may be tuned according to the type of target particles. For example, the field may take the values of the saturated field, $B_{SAT}$ and $-B_{SAT}$ (or North/South), for example in those magnetic flux concentrators comprising hard magnetic materials (the remanence for hard magnetic materials is close to, or the same value as, the saturation magnetization). Hence, the field can be usually switched between two opposite (saturated) polarities in normal operation. A step of demagnetization of the flux concentrator is also possible, for example at the start or end of a measurement cycle. The magnetic field may also take values within a range, which may be easily implemented in case of magnetic flux concentrators using soft magnetic materials. In typical applications of cell sorting, the magnetic field may take a value higher than 0.1 T, for example higher than 0.5 T.

The present disclosure may be applied to selection between multiple particle types. This may be obtained by pulsing the magnetic field at a plurality of, for instance two, different frequencies and a plurality of, for instance two, different amplitudes, thus creating different displacements based on a plurality of, for instance two, types of particles (for example, two target particles comprising different types or different amounts of attached MBs). In this case, at least two bifurcations may be provided for separating different target particles, for instance one bifurcation for each target particle (for example, comprising two selection ducts, for example of the same or different size). The method may also be used for separation of unattached MBs from tagged cells. Two separate magnetic flux concentrators associated with one selection duct each may also be used along the same main microfluidic channel for separating two different target particles.

In an "ideal" solution of target particles using MBs, all MBs would bind only to target particles, no MB would be loose and non-target particles would have no MB attached. In practice, as schematized in FIG. 1, a solution may comprise target particles 120, tagged by MBs, and may also contain loose MBs 121, non-target particles 122 and mistagged particles 123. The type of MB may be chosen according to the affinity with the target particle, so a large amount of target particles are tagged and the amount of mistagged particles is small, but not negligible, and these should be discriminated. The magnetic field in the region of the microfluidic channel next to the pole 111 enhances the movement of particles with a high number of MBs attached (a target particle) towards the selection duct 102 following the curved arrow 106, and non-tagged particles 122 are not deviated. The magnetic field is pulsed with a frequency and amplitude, which can be tuned so that other magnetic particles, like loose unattached MBs or mistagged particles, are differently affected by the pulses than the target particles due to, for example, the smaller volume (in case of loose MBs) or due to the fewer number of MBs attached, hence having different rate of movement across the liquid medium, making loose MBs and mistagged particles less likely to be deviated.

After the selection, the target may be further processed, for example they may be sent to a separator, a spectrometer, or a counter such as counters comprising induction coils, spin valve counters, superconducting quantum interference devices (SQUIDs), and solid state magnetic sensors, such as integrated tunneling or giant magnetoresistive (TMR, GMR) sensors or Hall sensors.

In cytometric applications relating oncology, for example in detection of a circulating tumour cell (CTC), hundreds of MBs may be attached to the CTC. For standard microchannels and at a flow rate typically used in known microfluidic devices (e.g. 0.1 mm/s), if the area of the flux concentrator (the pole) is 100 μm pole area, the time a particle flows over a pole region is 0.1 s. If the MB relaxation time is shorter than 1 μs, the magnetic field may be pulsed with a frequency of 1 MHz at 1 T, for example. The exact values may be tuned according to each particular case, for example by estimating the average momentum of the target particles in the fluid and tuning the frequency and amplitude of the magnetic field (or only the frequency, if the flux concentrator comprises hard magnetic materials, hence allowing the magnetic field to easily alternate between the values of magnetic saturation only).

The present disclosure is not limited to CTCs, and may be applied to virus, DNA, proteins, iron-bearing molecules, or any other molecule that may be conferred magnetic properties.

The size of the MBs may be higher than 10 nm, for example between 20 nm and 20 μm (micrometers), and in general they may be smaller than the target particles, which usually may accept a high number of MBs. The binding of MBs may be done via lectins, aptamers, receptors, direct or indirect coupling, for example via streptavidin-biotin interactions, for example via antibodies.

The microfluidic channels according to a first aspect of the present disclosure may be obtained by standard etching, or optical lithography, ion milling, ion etching, for example by standard semiconductor processing (e.g. CMOS processing) on a substrate, which may comprise polymer, glass, silicon or other semiconductor, etc. For example, the whole device may be compact, allowing circuit integration.

The invention claimed is:
1. A microfluidic magnetic selector comprising:
a microfluidic channel comprising a bifurcation, which splits the microfluidic channel into at least a selection channel;
a magnetic flux concentrator for concentrating a magnetic flux at a level of the bifurcation;

a means for generating a magnetic field through the magnetic flux concentrator, wherein the means for generating a magnetic field comprises coils that at least partially wound around both (i) the magnetic flux concentrator and (ii) the selection channel;

a current pulse generator that is connected to the coils, wherein the current pulse generator provides current pulses through the coils to generate magnetic pulses through the magnetic flux concentrator; and a controller that is connected to the current pulse generator, wherein the controller controls the current pulse generator to provide the current pulses through the coils.

2. The microfluidic magnetic selector of claim 1, wherein the magnetic flux concentrator comprises a ferromagnetic material with a saturation magnetization of at least 0.5 Tesla.

3. The microfluidic magnetic selector of claim 1, wherein the magnetic flux concentrator comprises a tip with a dimension between 10 nm and 0.1 mm.

4. The microfluidic magnetic selector of claim 1, wherein a connection between the microfluidic channel and the selection channel comprises the magnetic flux concentrator.

5. The microfluidic magnetic selector of claim 1, wherein the coils comprise conducting coils.

6. The microfluidic magnetic selector of claim 1, wherein the microfluidic channel is configured to convey a fluid comprising at least one target particle exhibiting superparamagnetic, ferromagnetic or paramagnetic behavior in presence of a magnetic field.

7. The microfluidic magnetic selector of claim 6, wherein the at least one target particle is linked to at least one ferromagnetic, superparamagnetic or paramagnetic bead.

8. The microfluidic magnetic selector of claim 1, wherein the magnetic pulses comprise the magnetic field varying between at least two pre-determined values of amplitude, frequency, or pulse width.

9. The microfluidic magnetic selector of claim 1, wherein the magnetic flux concentrator comprises a hard magnetic material.

10. The microfluidic magnetic selector of claim 9, wherein the hard magnetic material comprises at least one of: CoFe or CoFeB.

11. The microfluidic magnetic selector of claim 1, wherein the magnetic pulses are generated at a frequency within an inclusive range between 0.1 MHz and 1 GHz.

12. The microfluidic magnetic selector of claim 1, wherein the generated magnetic pulses each having a pulse width that is the same or higher than a relaxation time of a target particle flowing in a fluid within the microfluidic channel.

* * * * *